(12) United States Patent
Cui et al.

(10) Patent No.: US 9,579,204 B2
(45) Date of Patent: Feb. 28, 2017

(54) SURGICAL IMPLANTS

(71) Applicant: OXFORD MESTAR LIMITED, Oxfordshire (GB)

(72) Inventors: Zhanfeng Cui, Oxfordshire (GB); Phillipus Johannes Putter, Suffolk (GB); Michael Tian-Ao Cui, Oxfordshire (GB)

(73) Assignee: OXFORD MESTAR LIMITED, Oxfordshire (GB)

( * ) Notice: Subject to any disclaimer, the term of this patent is extended or adjusted under 35 U.S.C. 154(b) by 0 days.

(21) Appl. No.: 14/795,991

(22) Filed: Jul. 10, 2015

(65) Prior Publication Data

US 2017/0007406 A1    Jan. 12, 2017

(51) Int. Cl.
| | | |
|---|---|---|
| *A61F 2/30* | (2006.01) | |
| *A61F 2/02* | (2006.01) | |
| *A61F 2/28* | (2006.01) | |
| *B33Y 10/00* | (2015.01) | |
| *B33Y 80/00* | (2015.01) | |

(52) U.S. Cl.
CPC . *A61F 2/28* (2013.01); *A61F 2/02* (2013.01); *A61F 2/30942* (2013.01); *A61F 2002/30062* (2013.01); *A61F 2002/3096* (2013.01); *A61F 2002/30387* (2013.01); *A61F 2002/30604* (2013.01); *A61F 2002/30962* (2013.01); *B33Y 10/00* (2014.12); *B33Y 80/00* (2014.12); *Y10T 29/49861* (2015.01)

(58) Field of Classification Search
CPC .......... A61F 2/28; A61F 2/30942; A61F 2/02; A61F 2002/30062; A61F 2002/30387; A61F 2002/30604; A61F 2002/3096; A61F 2002/30962; Y10T 29/49861; B33Y 10/00; B33Y 80/00
See application file for complete search history.

(56) References Cited

U.S. PATENT DOCUMENTS

| | | | | |
|---|---|---|---|---|
| 5,344,461 | A * | 9/1994 | Phlipot | A61F 2/4684 623/20.16 |
| 2012/0271418 | A1 | 10/2012 | Hollister et al. | |
| 2013/0138214 | A1* | 5/2013 | Greenhalgh | A61F 2/4455 623/17.16 |
| 2015/0374450 | A1* | 12/2015 | Mansfield | A61B 34/10 264/219 |

FOREIGN PATENT DOCUMENTS

CN            103977451 A      8/2014

* cited by examiner

*Primary Examiner* — John C Hong
(74) *Attorney, Agent, or Firm* — Saul Ewing LLP

(57) ABSTRACT

A method of constructing a surgical implant is provided. The method comprises providing a multiplicity of substantially identical blocks, each having features thereon to allow blocks to be mechanically joined together. A surgical implant may then be constructed by using these features to join the blocks together into a desired configuration.

14 Claims, 11 Drawing Sheets

SURGICAL IMPLANTS

TECHNICAL FIELD

The present invention relates to surgical implants and to a method of constructing surgical implants. More particularly, though not necessarily, the invention relates to tissue scaffolds and their construction.

BACKGROUND

This section is intended to provide background or context to the invention recited in the claims. The description of the background art may include insights, discoveries, understandings or disclosures, or associations of disclosures not known in the prior art. Some contributions of the invention may be specifically pointed out below, whereas other contributions of the invention will be apparent from their context.

Surgical implants such as degradable tissue scaffolds can be used to fill defects in soft tissue or bone. These defects may be caused by removal of a tumour, or by bone or cartilage loss in a hip or knee replacement procedure, for example. Orthopaedic tissue engineering is a field concerned with the development of tissue scaffolds which are used to treat injuries or diseases in bone, and which are compatible with the patient's own biology. Tissue scaffolds may be utilised for both humans and animals.

Orthopaedic injuries or diseases vary significantly on a case by case basis. Highly invasive surgical procedures such as hip replacements can result in significant bone loss, leaving a defect in the bone. Each patient is different, not only in the size of the bone in question but also in the dimensions of the defect. Custom built scaffolds may therefore be desirable. However, their design and manufacture can be extremely expensive. The patient concerned must undergo detailed MRI or CT scans, which must be interpreted by both a surgeon and a tissue engineer with 3D modelling experience. The tissue scaffold must then be manufactured in advance of the surgery, at significant cost to the patient or to the healthcare provider.

FIG. 1 shows a degradable polymer tissue scaffold produced in line with recent developments, as discussed above. Computed tomography (CT) imaging data was used to reconstruct a defect in the jaw of a dog with an aggressive type of bone cancer. After designing a scaffold to fill the defect using the CT imaging data, a polymer implant was fabricated using 3D printing techniques. FIG. 2 illustrates the same implant as it appears when implanted in the jaw. The implant is located towards the left hand side of the jaw.

Recent developments in the manufacture of tissue scaffolds utilise 3D printing. For example, CN103977451 discloses a 3D printing manufacturing method for an artificial bone scaffold. However, even where customer scaffolds are produced from scan data and accurately manufactured by a technique such as 3D printing, they still do not always fit accurately. US2012/0271418 describes a biocompatible and implantable tissue scaffold having a modular design comprising a tissue scaffold rack designed to accommodate one or more modules.

SUMMARY OF THE INVENTION

It is an object of the present invention to provide a simple and flexible process for constructing surgical implants, for example in an operating theatre, which overcomes many of the problems associated with pre-constructed implants, even when such pre-constructed implants have a modular construction.

According to a first aspect of the invention, there is provided a method of constructing a surgical implant. The method comprises providing a multiplicity of blocks having substantially identical cross-sections, each block having features thereon to allow the blocks to be mechanically joined together, and constructing a surgical implant by using said features to join the blocks together into a desired configuration.

The method may provide advantages over known methods of surgical implant construction, since it enables rapid construction and re-configuration of an implant to cope with unexpected events or irregularities in the surgical process.

The constructing step of the method may further comprise cutting the joined blocks to a desired shape, prior to incorporating them into the structure.

The blocks may comprise a biocompatible and biodegradable polymer, optionally polylactic acid.

The features may comprise interlocking male tabs and corresponding female slots. For example, the features may comprise dovetail joints.

The blocks may be substantially identical in all dimensions. The substantially identical blocks may be substantially cuboid. The method may further comprise providing one or more additional non-identical blocks, but with substantially the sam-cross-sections, each having features thereon to allow them to be joined together and/or to substantially identical blocks. Such non-identical blocks may function as edging or end blocks.

The surgical implant may be an orthopaedic tissue scaffold.

Each block may comprise joining features on all surfaces.

According to a second aspect of the invention, there is provided a surgical implant constructed using a multiplicity of blocks having substantially identical cross-sections, mechanically interconnected together by means of features provided on the blocks.

The substantially identical blocks may be porous. The implant may be a tissue scaffold. The blocks may be biodegradable.

The blocks may be substantially identical in all dimensions. The multiplicity of substantially identical blocks may have been cut to different sizes.

According to a third aspect of the invention, there is provided a kit for constructing a surgical implant. The kit comprises a multiplicity of substantially identical blocks each having features thereon to allow blocks to be mechanically joined together.

According to a fourth aspect of the invention there is provided a method of performing re-constructive surgery on a patient. The method comprises providing a multiplicity of substantially identical blocks each having features thereon to allow blocks to be mechanically joined together; constructing a surgical implant by using said features to join the blocks together into a desired configuration and implanting the surgical implant into the patient.

The method may further comprise cutting at least some of the blocks to size prior to the step of constructing the surgical implant.

According to a fifth aspect of the invention, there is provided a method of constructing a surgical implant. The method comprises providing a multiplicity of substantially identical blocks each having features thereon to allow blocks to be mechanically joined together; cutting at least some of the blocks to a desired size, and constructing a surgical implant by using said features to join the blocks together into a desired configuration.

According a further aspect of the invention there is provided a kit for constructing a tissue scaffold and comprising a multiplicity of porous blocks each having a generally cuboid shape and each having features thereon to allow blocks to be mechanically joined together. The cross-sectional shapes of the blocks may be substantially identical.

DETAILED DESCRIPTION

A method will now be described which can be used to construct a surgical implant. The method allows an implant, such as a tissue scaffold, to be constructed by joining together a multiplicity of blocks in order to form a scaffold of the correct size and shape for the defect concerned. This scaffold may be used to fill or bridge defects in bone, soft tissue or cartilage. The scaffold may be configured to induce bone or tissue growth and may be porous and biodegradable.

Figure 1:
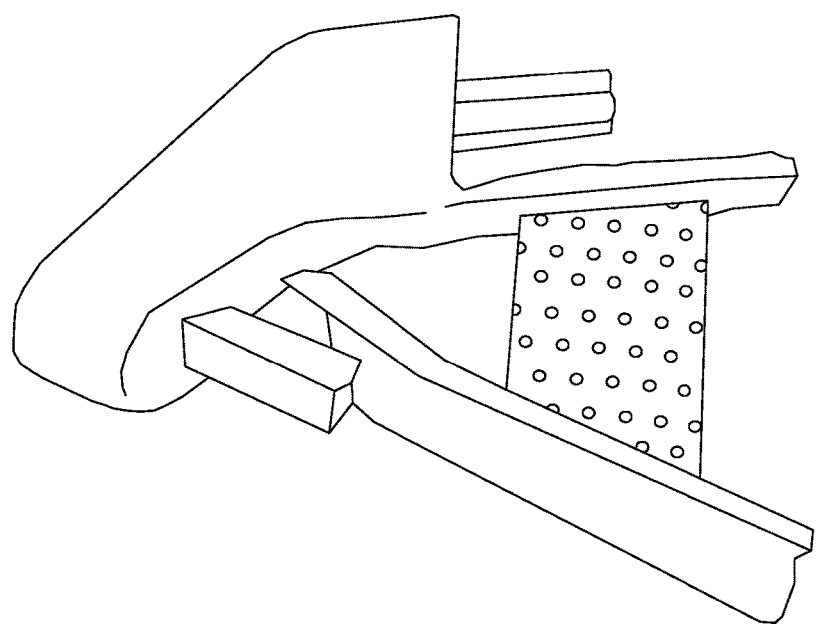
FIG. 1 is a perspective view of a conventional scaffold produced using imaging data and manufactured using 3D printing.
Figure 2:
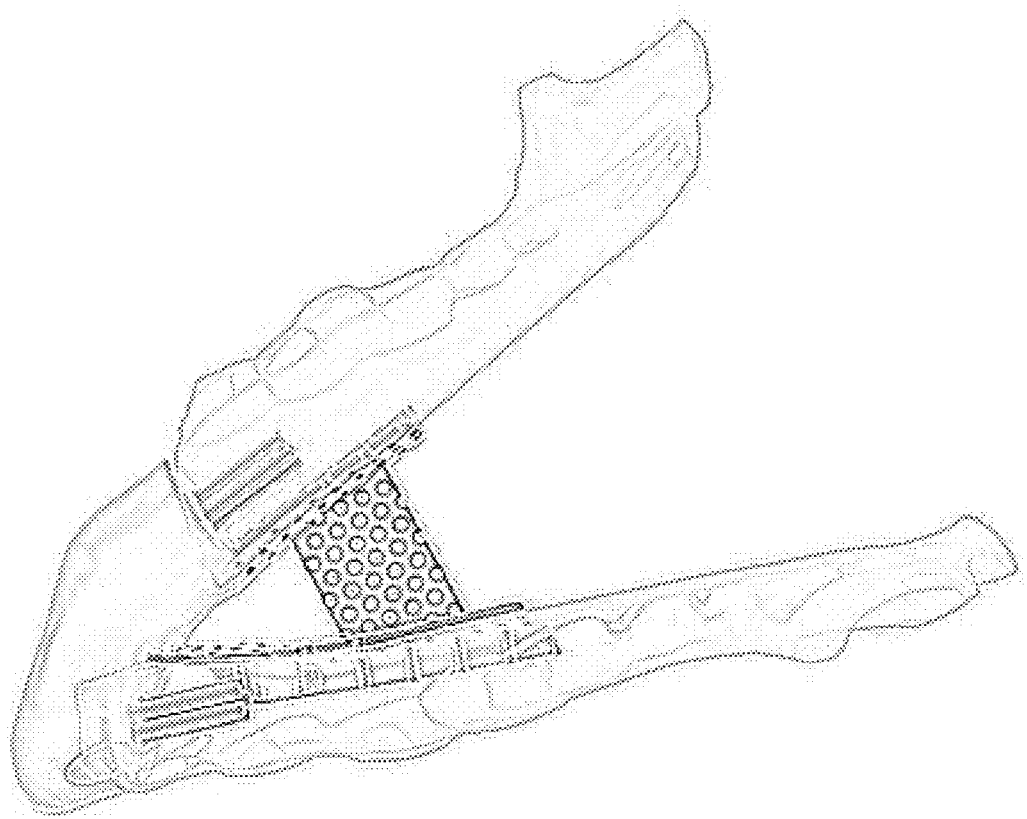
FIG. 2 is a model of the scaffold of FIG. 1 implanted in a jaw.
Figure 3:
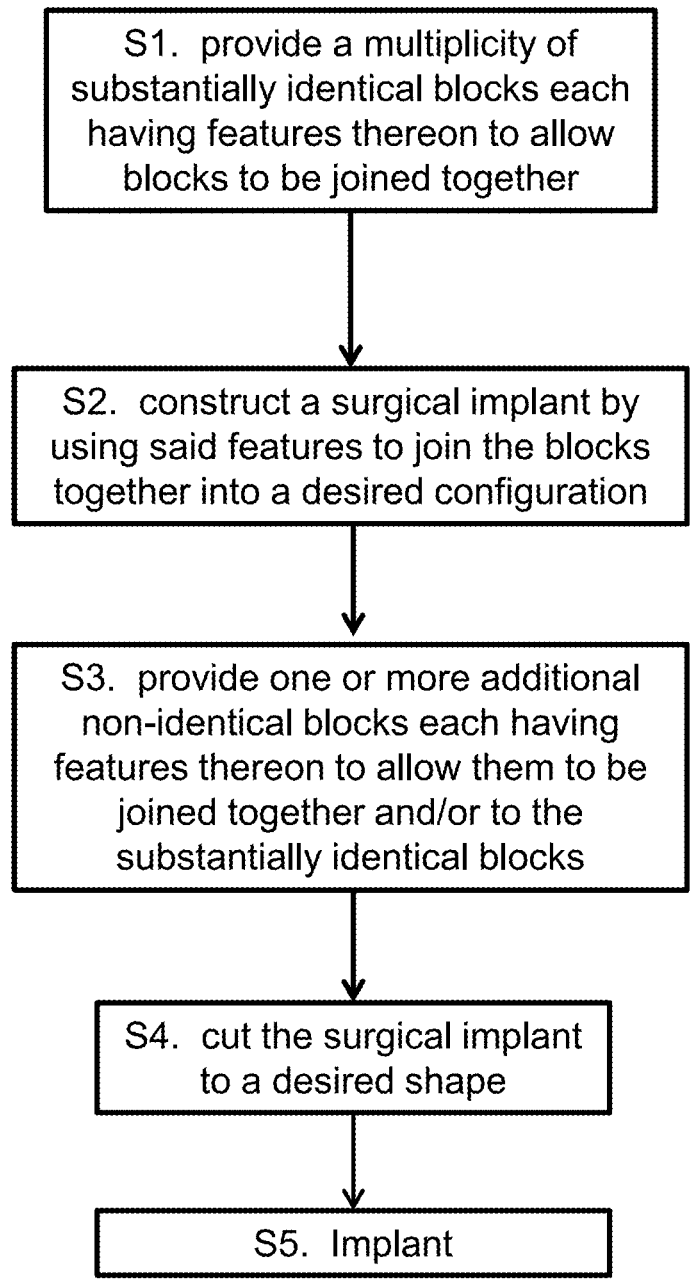
FIG. 3 is a diagrammatic representation of a method of constructing a surgical implant.

FIG. 3 is a diagrammatic representation of a method of constructing and implanting a surgical implant, the method comprising the following steps:

S1: providing a multiplicity of substantially identical blocks each having features thereon to allow blocks to be joined together;

S2: constructing a surgical implant by using said features to join the blocks together into a desired configuration.

S3: providing one or more additional non-identical blocks each having features thereon to allow them to be joined together and/or to the substantially identical blocks;

S4: cutting the surgical implant to a desired shape.

S5: The implant is implanted into a patient.

In step S1, a number of substantially identical blocks are provided. The blocks may be manufactured by any suitable means, for example, by 3D printing. In this context, 3D printing is a method of additive manufacture whereby a three-dimensional model is used to create a physical three-dimensional object. The exact method may vary, but by far the most prevalent method is multilayer deposition, where any object is built up layer by layer. Other techniques include laser sintering and laser crosslinking. The blocks may be manufactured as needed within the surgery, hospital or other clinical environment, or may be manufactured elsewhere and stored until required.

The identical blocks are manufactured from a biocompatible material, and where 3D printing is used in their manufacture, from a material which is suitable for use in this process. For 3D printing, the material must be a liquid or a very soft solid when deposited. Where a polymer is used, this must be able to melt and re-solidify relatively easily. Viscoelastic materials can also be deposited in 3D printing techniques. Polymers commonly used in 3D printing include polylactic acid (PLA) and acrylonitrile butadiene styrene (ABS). PLA is a common biocompatible material which melts at approximately 180° C. and so is particularly suitable for block manufacture.

The blocks in this example are substantially cuboid in design and each of the blocks has features which allow the blocks to be joined together. In this example, these features are dovetail joints which allow the blocks to interlock, providing a mechanically stable structure. It will be appreciated that the identical nature of the blocks and the simplicity of their design enables the blocks to be easily and quickly manufactured by, for example, a 3D printing process.

In step S2, a surgical implant is constructed by using said features to join the blocks together into a desired configuration. As previously discussed, conventional scaffolds are typically designed using imaging data, for example from MRI or CT scans of the patient. Obtaining and analysing this data in order to design an accurate and detailed scaffold model is a complex, expensive and often lengthy process.

Conversely, the modular blocks provided by the method herein described are simple interlocking blocks which can be quickly manufactured and subsequently joined together into any desired configuration. Hence, an implant (such as a scaffold) of suitable size and shape may be constructed by a clinician, surgeon or the like before or during the procedure during which a defect is created or filled, possibly even within the operating theatre itself. The implant may be designed and constructed at short notice without the need for imaging data or software.

It will be appreciated that the construction of the implant may be a matter of trial and error, during which blocks may be added, removed or moved as required, until a suitable and accurate scaffold structure is formed. For example, if it is discovered that an implant is too big or too small, the implant can be shortened or lengthened as required by simply removing or adding one or more blocks. The ability to configure and reconfigure the structure as required is made possible by the blocks being substantially identical.

In step S3, one or more additional non-identical blocks are optionally provided each having features thereon to allow them to be joined to the substantially identical blocks. These additional blocks are not identical to the blocks provided in step S1. They may comprise corner blocks, centre blocks, end blocks, capping blocks, double height or double width blocks or any other type of block which may be joined to or included in the structure formed by one or more of the identical blocks. The additional blocks may comprise at least one surface which does not comprise a joining feature. The additional blocks may also be manufactured by a 3D printing technique and may comprise a degradable, biocompatible polymer, optionally polylactic acid.

In step S4, the surgical implant may be optionally cut to a desired shape if deemed necessary. The method herein described may include step S4 with or without step S3, described above. After joining two or more substantially identical blocks together to form a surgical implant, the structure may be further cut to shape, for example using a saw or other suitable cutting or trimming apparatus or methods. This cutting may smooth the exterior of the implant or may impart a desired shape or configuration to the implant. For example, joining features on the blocks which form the exterior wall of the implant may be cut away or trimmed. Cutting should not alter the internal porous structure of the scaffold. Alternatively, an interior of the implant may be cut to form voids or apertures as required. Where additional non-identical blocks form part of the implant structure, these may also be cut or trimmed.

Figure 4:
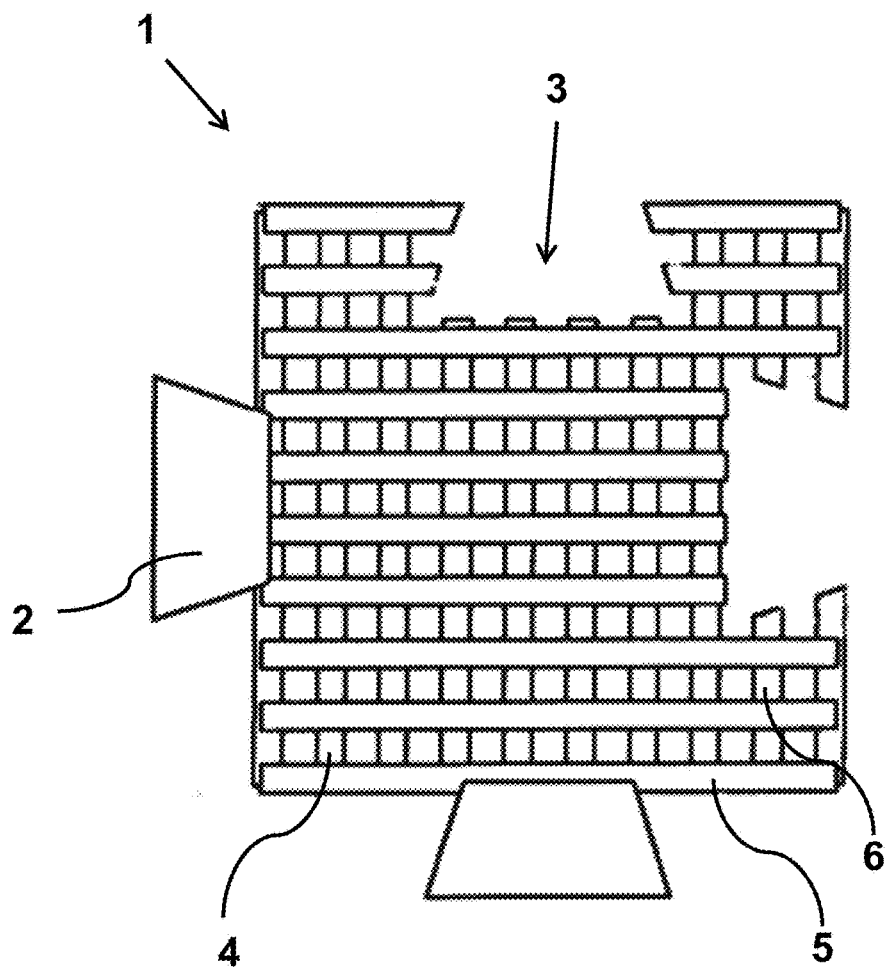
FIG. 4 is a plan view of an example of a block for use in the method of FIG. 3.
Figure 5:
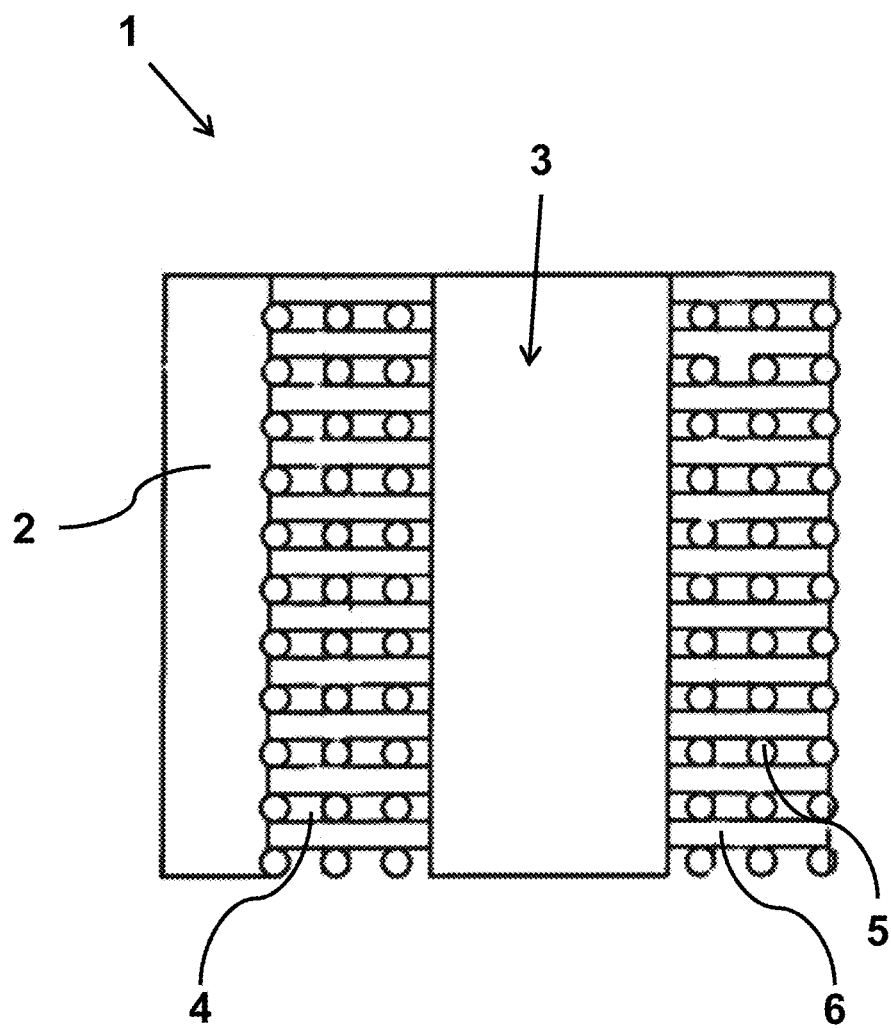
FIG. 5 is a side view of the block of FIG. 4.
Figure 6:
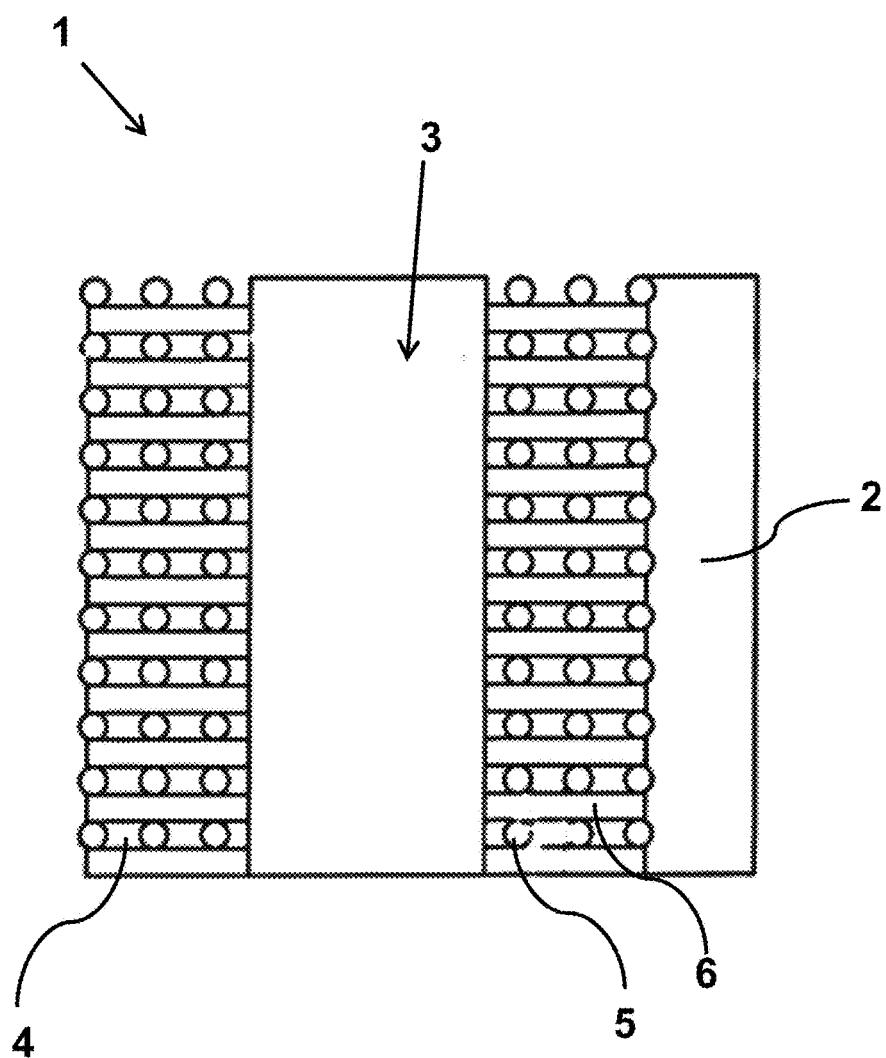
FIG. 6 is a further side view of the block of FIG. 4.
Figure 7A:
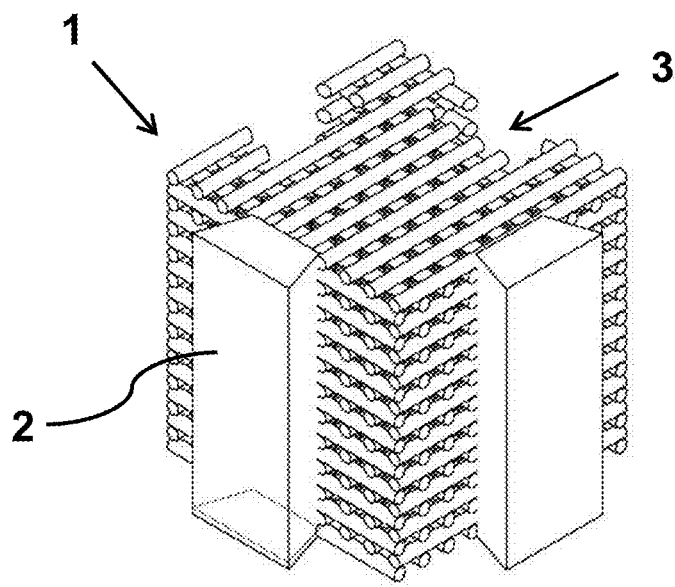
FIG. 7a is a perspective view of a porous block for use in the method of FIG. 3.

FIGS. 4 to 6 are plan and side views of an exemplary porous block 1 for use in the method described with reference to FIG. 3 above. FIG. 7a provides a perspective view of a porous block, for use in the method of FIG. 3. The block 1 in this example is essentially cuboid and is provided with joining features 2, 3 on four faces. Two of these features are male joining features 2, comprising protruding tabs or tongues and two are corresponding female joining features 3, comprising slots or pockets. A male joining feature 2 from a first block may be joined to a female joining feature 3 of a second block and so on. It will be understood that one block may be joined to one, two, three, four or more further blocks in this way.

In this example, the joining features comprise dovetail joints in which the male joining features 2 slide into the female joining features 3, forming a mechanically stable joint. A number of modular blocks 1 may be supplied in a set. The set may also include additional non-identical blocks as described above. A surgical implant, such as an orthopaedic tissue scaffold, may then be constructed from the set of blocks. In order to provide additional flexibility, joining features may be provided on all six surfaces of the blocks, not just on four surfaces as shown.

The block 1 shown in this example has a porous construction. Multiple apertures 4 are formed by a lattice of multiple horizontal 5 and vertical cross members 6. The porosity of the blocks 1 and therefore the scaffold enables adjacent cells to grow into the scaffold and hence promotes tissue regrowth. It will be appreciated that 3D printing is particularly suited to the production of such porous structures, something that is particularly difficult to achieve with conventional plastics moulding processes.

Figure 7B:
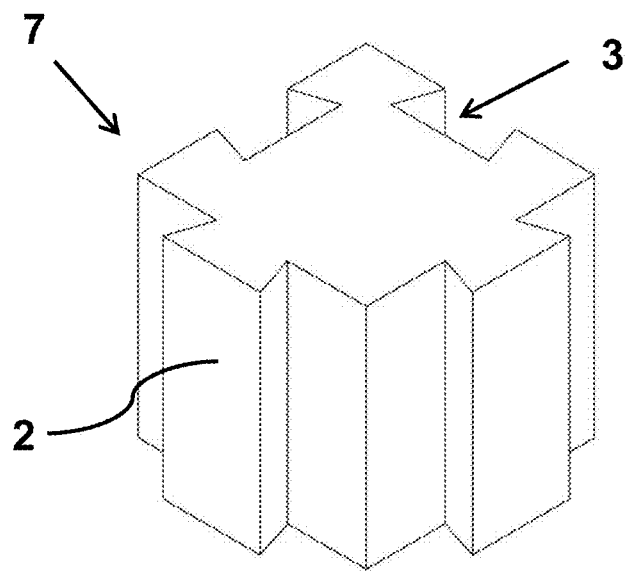
FIG. 7b is a perspective view of a non-porous block for use in the method of FIG. 3.

The block 7 shown in FIG. 7b is of substantially identical dimensions to the block shown in FIG. 7a, but has a non-porous, solid construction.

Figure 8:
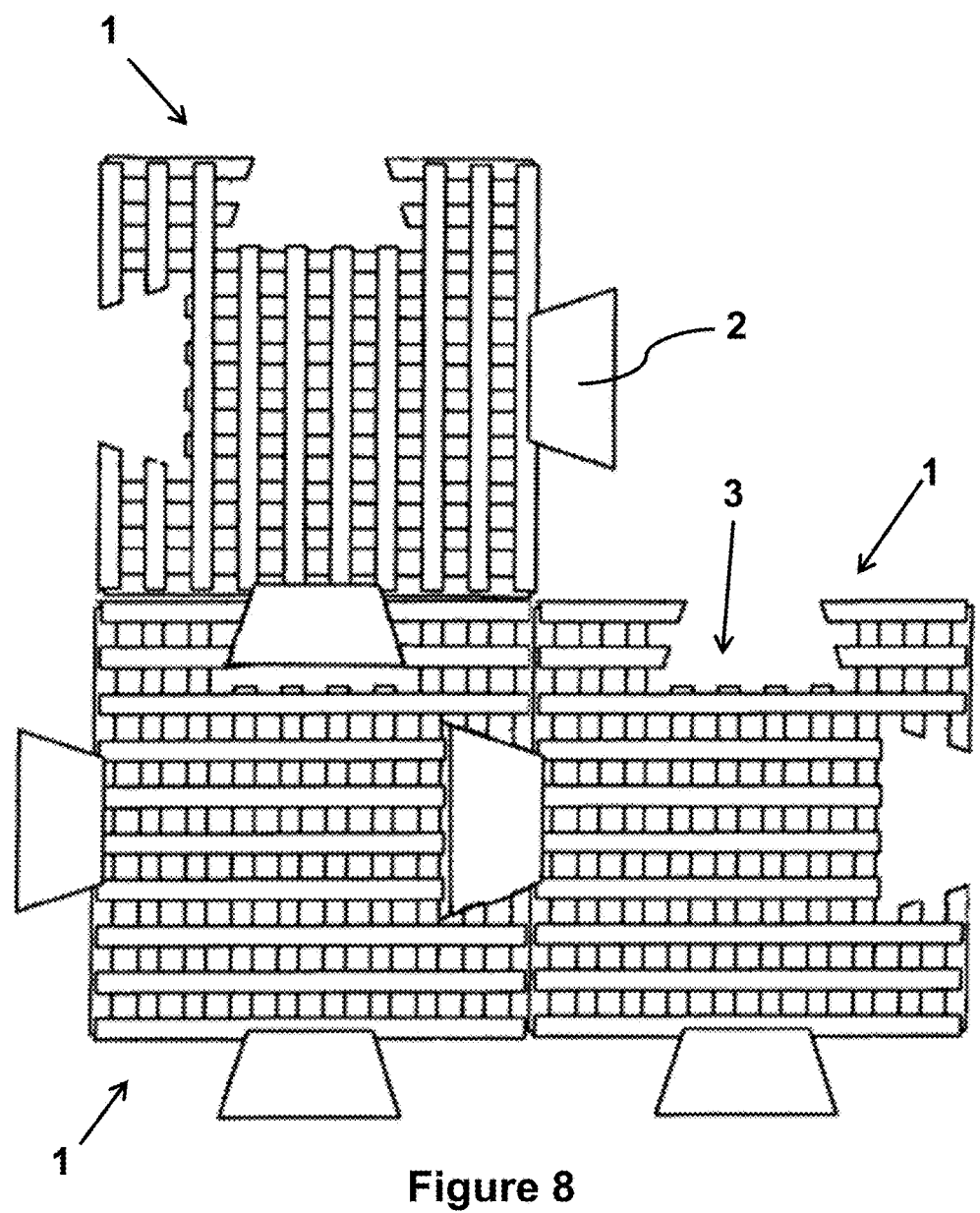
FIG. 8 is a plan view of several blocks for use in the method of FIG. 3, joined together.

FIG. 8 is a plan view of a number of substantially identical porous blocks 1 joined together. In this way, a desired implant structure may be built up by joining a number of blocks 1, as required by the dimensions of the defect to be filled. The substantially trapezoidal male 2 and female 3 joining features co-operate to form a mechanically stable dovetail joint. Since the male joining feature 2 slides into the female joining feature 3, the joint will resist forces which would separate blocks held together by other means, for example, by snap fit connectors. Similarly, the joint will withstand compressive forces whilst maintaining the overall structure of the implant.

It will also be appreciated that the blocks 1 described herein are quick and easy to connect together and require no additional tools or equipment. Since the jointing features 2, 3 are integral no separate connectors are needed. As each block 1 is substantially identical, the blocks 1 can be easily interchanged. For example, should one block 1 become damaged or incorrectly trimmed, it can be exchanged for another identical block 1. The substantially cuboid block shape is easy to handle and allows an implant structure to be built up quickly. The cuboid shape is also resistant to deformation, both during the implant procedure and after it is complete.

Additionally, the substantially identical blocks 1 once joined together as herein described are self-supporting. The use of a supporting structure, such as a tray or rack, or of an outer cover or container to hold the blocks in place, is therefore obviated.

Figure 9:
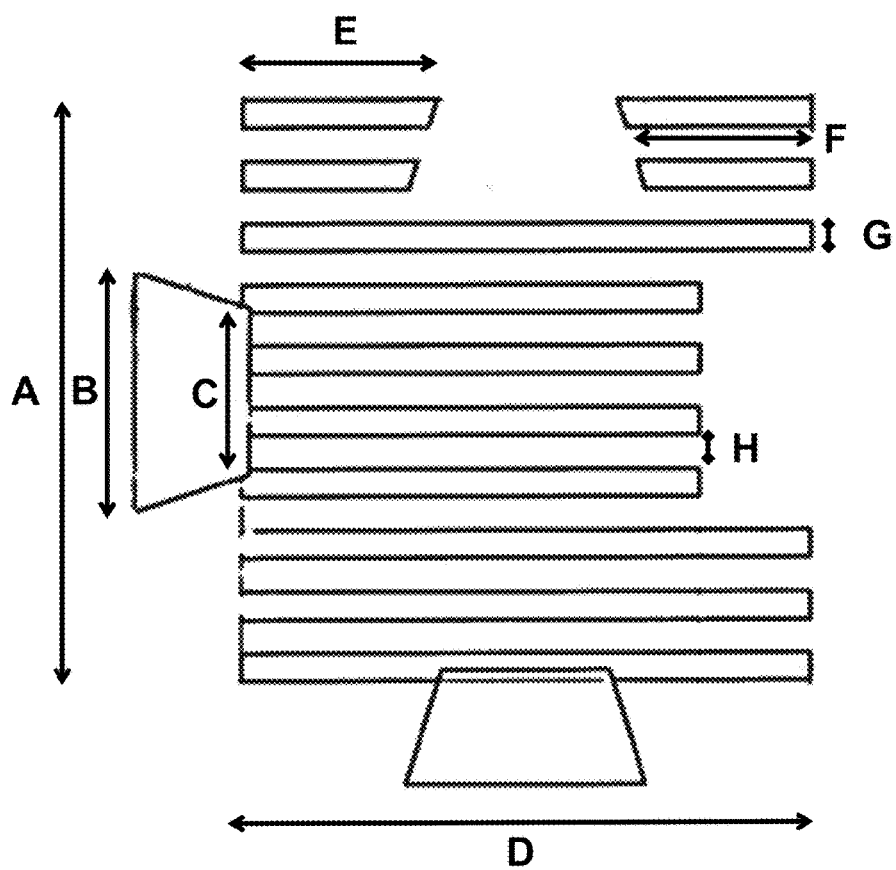
FIG. 9 is a representation of a block for use in the method of FIG. 3 showing scale.
Figure 10:
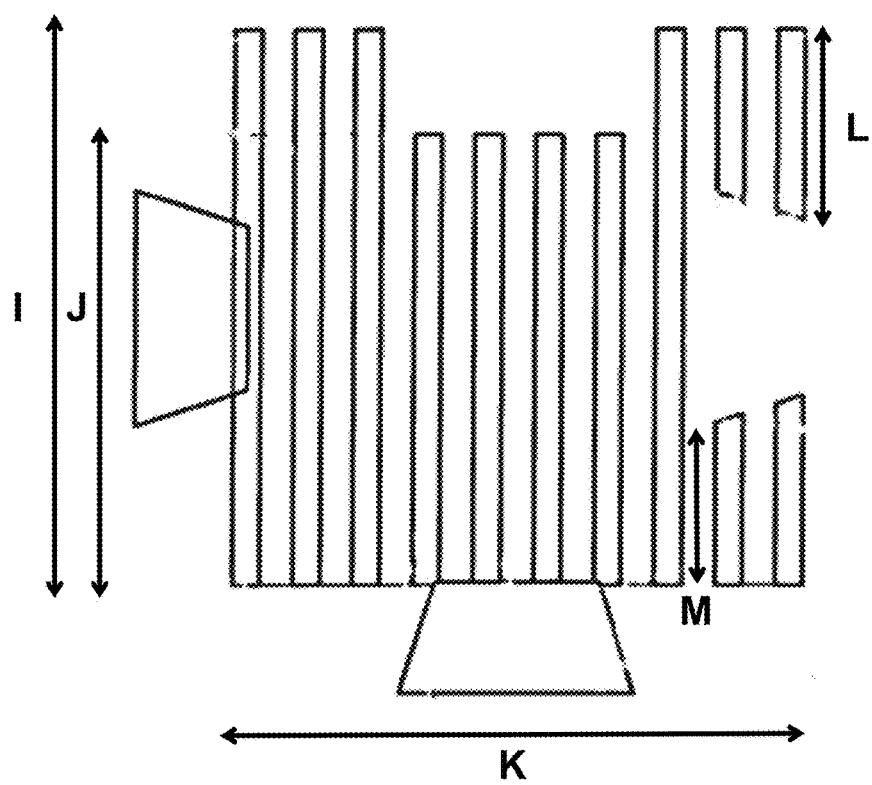
FIG. 10 is a further representation of a block for use in the method of FIG. 3, showing scale.

FIGS. 9 and 10 are further representations of blocks for use in the method described in relation to FIG. 3. Certain parts of the block are not shown in order to facilitate understanding of the exemplar block dimensions, which are as follows:

Length A is around 8.40 mm;
Length B is around 3.47 mm;
Length C is around 2.41 mm;
Length D is around 8.20 mm;
Length E is around 2.80 mm;
Length F is around 2.52 mm;
Length G is around 0.40 mm;
Length H is around 0.49 mm;
Length I is around 8.20 mm;
Length J is around 6.65 mm;
Length K is around 8.40 mm;
Length L is around 2.81 mm;
Length M is around 2.40 mm.

From the above it will be appreciated that each block is substantially a cube measuring around 10 mm by 10 mm by 10 mm overall and provided with both male jointing features in the form of tabs or tongues and female jointing features in the form of corresponding slots or pockets. The block dimensions are optimised to enable detailed and complex implants to be built up which will fit snugly into defects of various sizes, while also providing ease of handling.

Figure 11:
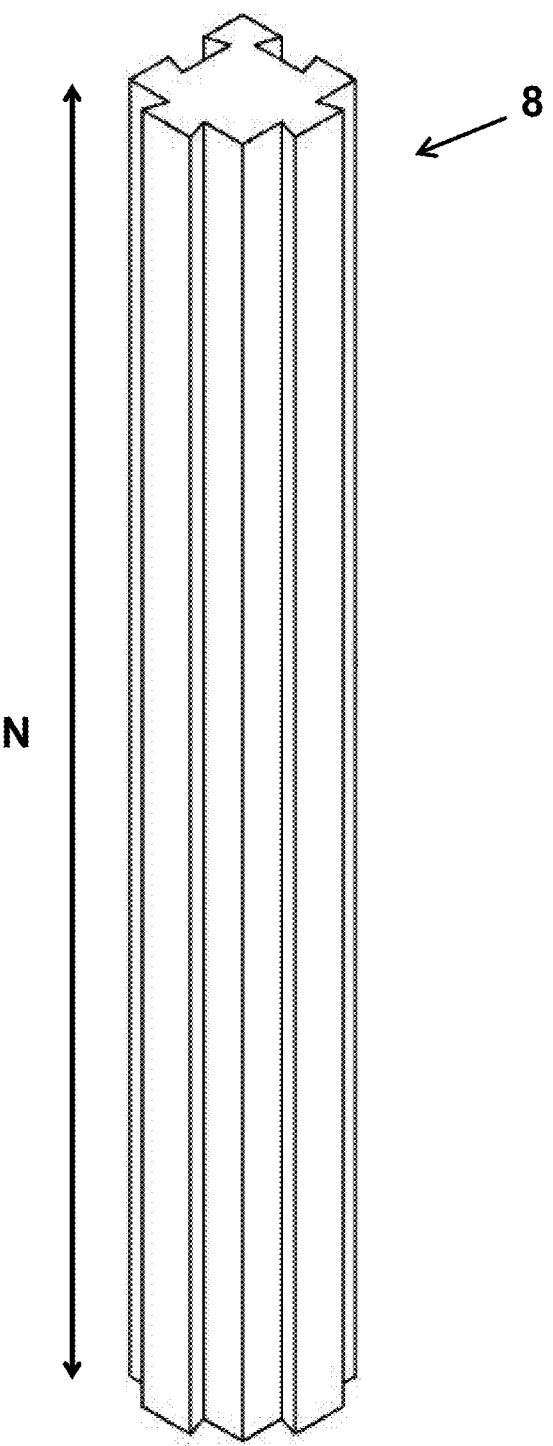
FIG. 11 is a perspective view of a block of increased height.

An alternative means to achieve an implant of varying thickness is to make use of blocks having increased height. These can then be cut down to size depending upon the requirements, resulting in the use of multiple blocks having different heights. FIG. 11 illustrates a block 8 which has a height N of 84 mm. Apart from the block's increased height, its other dimensions are substantially similar to the block illustrated in FIGS. 9 and 10.

It will be appreciated by the person of skill in the art that various modifications may be made to the above described examples or embodiments and/or one or more features of the described examples or embodiments may be combined without departing from the scope of the present invention.

For example, the substantially identical blocks may be solid rather than porous in construction. Where a porous block is used in the method described herein, the pores may vary in size depending upon the required application. The pores may be substantially square, circular or irregular in shape. The block may be partially porous.

The dimensions of the substantially identical blocks may vary, and the blocks may not necessarily be cuboid. For example, the height of each block may be a multiple of its length, such as twice or three times its length, or vice versa. Alternatively, the blocks may be circular or irregular in shape.

The joining features of the substantially identical blocks may comprise other arrangements which provide a mechanical joint. The male and female jointing features may be circular or irregular in shape rather than trapezoid.

What is claimed is:

1. A method of constructing a surgical implant comprising:
   providing a multiplicity of blocks having substantially identical cross-sections, each block having features thereon to allow the blocks to be mechanically joined together; and
   constructing a surgical implant by using said features to join the blocks together into a desired mechanically stable configuration which substantially prevents relative movement of adjacent blocks.

2. A method as claimed in claim 1, further comprising manufacturing the blocks by 3D printing.

3. A method as claimed in claim 1, wherein said step of constructing further comprises cutting the joined blocks to a desired shape.

4. A method as claimed in claim 1, wherein the blocks are porous.

5. A method as claimed in claim 1, wherein the blocks comprise a biocompatible and biodegradable polymer.

6. A method according to claim 5, wherein said biocompatible and biodegradable polymer is polylactic acid.

7. A method as claimed in claim 1, wherein the features comprise interlocking male tabs and corresponding female slots.

8. A method as claimed in claim 1, wherein the features comprise dovetail joints.

9. A method as claimed in claim 1, wherein said multiplicity of blocks are substantially identical.

10. A method as claimed in claim 9, further comprising providing one or more additional non-identical blocks each having features thereon to allow them to be joined together and/or to said substantially identical blocks.

11. A method as claimed in claim 1, wherein the surgical implant is an orthopaedic tissue scaffold.

12. A method as claimed in claim 1, wherein the said blocks are substantially cuboid having a plurality of surfaces.

13. A method according to claim 12, wherein each said block comprises joining features on all surfaces.

14. A method according to claim 1 and comprising cutting at least some of the blocks to size prior to said step of constructing the surgical implant.

* * * * *